United States Patent [19]

Fujii et al.

[11] E Re. 31,245

[45] Reissued May 17, 1983

[54] PROCESS FOR PREPARING A DIESTER OF OXALIC ACID IN THE GASEOUS PHASE

[75] Inventors: Kozo Fujii; Keigo Nishihira; Masaoki Matsuda; Shinichiro Uchiumi, all of Ube, Japan; Kenji Nishimura, deceased, late of Ube, Japan, by Yoko Nishimura, administrator

[73] Assignee: UBE Industries, Ltd., Ube, Japan

[21] Appl. No.: 293,932

[22] Filed: Aug. 18, 1981

Related U.S. Patent Documents

Reissue of:

[64] Patent No.: 4,229,591
Issued: Oct. 21, 1980
Appl. No.: 938,358
Filed: Aug. 31, 1978

[30] Foreign Application Priority Data

Jan. 25, 1978 [JP] Japan ..... 53-6150
Jan. 30, 1978 [JP] Japan ..... 53-8268

[51] Int. Cl.[3] ..... C07C 67/36; C07C 69/36

[52] U.S. Cl. ..... 560/193; 560/190; 560/204

[58] Field of Search ..... 560/190, 193, 204

[56] References Cited

U.S. PATENT DOCUMENTS 2,739,166 3/1956 Treacy .
4,138,587 2/1979 Yamasaki et al. ..... 560/204

FOREIGN PATENT DOCUMENTS 1156775 5/1964 Fed. Rep. of Germany .
2733730 2/1978 Fed. Rep. of Germany .
50-157311 12/1975 Japan .

OTHER PUBLICATIONS

Karrer; *Organic Chemistry,* p. 100 (1938).

*Primary Examiner*—Natalie Trousof
*Assistant Examiner*—Vera C. Clarke
*Attorney, Agent, or Firm*—Fisher, Christen & Sabol

[57] ABSTRACT

A process for preparing a diester of oxalic acid which comprises bringing carbon monoxide into contact with an ester of nitrous acid or with an alcohol and a nitrogen oxide or a hydrate of the nitrogen oxide in the gaseous phase in the presence of a solid catalyst containing metallic palladium or a salt thereof, a gas containing molecular oxygen being introduced into the reaction system in cases where said nitrogen oxide or a hydrate of the nitrogen oxide requires molecular oxygen together with the alcohol to form an ester of nitrous acid.

9 Claims, No Drawings

PROCESS FOR PREPARING A DIESTER OF OXALIC ACID IN THE GASEOUS PHASE

Matter enclosed in heavy brackets [ ] appears in the original patent but forms no part of this reissue specification; matter printed in italics indicates the additions made by reissue.

This invention relates to a process for preparing a diester of oxalic acid. More particularly, this invention relates to a process for preparing a diester of oxalic acid which comprises bringing carbon monoxide into contact with an ester of nitrous acid or with an alcohol and a nitrogen oxide or a hydrate of a nitrogen oxide in the gaseous phase in the presence of a solid catalyat containing metallic palladium or a salt thereof.

Diesters of oxalic acid have been used as important starting material for synthesizing oxalic acid, oxamide, glycols, intermediates for dyes, pharmaceuticals and so on.

There have hitherto been proposed various catalyst systems, co-catalysts, reaction accelerators and so on for a process for the preparation of a diester of oxalic acid which comprises reacting an alcohol with carbon monoxide, or a reacting them with molecular oxygen in the liquid phase under high pressure in the presence of a catalyst containing a platinum group metal. However, all of the conventional processes shown serious defects and hence have not been applied practically.

In view of the actual circumstances, the present inventors have made extensive studies for establishing an excellent process for preparing a diester of oxalic acid industrially. As a result, the present inventors have found that a diester of oxalic acid can be produced industrially with extreme advantage by bringing carbon monoxide into contact with an ester of nitrous acid or with an alcohol and a nitrogen oxide or a hydrate of a nitrogen oxide in the gaseous phase in the presence of a solid catalyst containing metallic palladium or a salt thereof, with introducing a gas containing molecular oxygen in cases where nitrogen monoxide is used. And thus the present invention has been accomplished.

According to the process of this invention there have been removed various defects in conventional processes which comprise subjecting an alcohol to catalytic oxycarbonylation reaction in the liquid phase, and a diester of oxalic acid can be produced industrially with extreme advantage.

Namely, the process of this invention has many advantages as mentioned below:

(i) It is possible to produce a diester of oxalic acid in high selectivity and in high space time yield even under ordinary pressure or reduced pressure, under which conditions a diester of oxalic acid has not substantially been produced by the liquid phase reaction which has conventionally been proposed. Accordingly, the present process requires no expensive high-pressure apparatus and reduces the power for the compression of the starting materials.

(ii) Since a solid catalyst is used on a fixed bed or a fluidized bed, the present process requires no special apparatus for separating the reaction products from the catalyst. Since the present process relies on the gaseous phase reaction, there is no loss of disolved palladium, which loss has frequently been observed in the conventional liquid phase reaction.

(iii) The solid catalyst is excellent in durability and accordingly has a long life.

Although the mechanism of the reaction which proceeds on the catalyst of this invention has not sufficiently been elucidated, the main reaction can be illustrated by the following equation.

$$2CO + 2RONO \longrightarrow \begin{array}{c} COOR \\ | \\ COOR \end{array} + 2NO$$

wherein R represents an alkyl group or a cycloalkyl group.

As seen from the equation, nitrogen monoxide equivalent to the consumed ester of nitrous acid is generated. Accordingly, the nitrogen monoxide thus formed may be recycled and used again as a starting material for preparing a diester of oxalic acid by recovering again as an ester of nitrous acid after introduction of an alcohol and a gas containing molecular oxygen to react them with the nitrogen monoxide according to the equation shown below.

$$2NO + \tfrac{1}{2}O_2 + 2ROH \rightarrow 2RONO + H_2O$$

[Wherein] *wherein* R is the same as defined above.

The nitrogen compound used in the present process need not necessarily be in the form of an ester of nitrous acid, and a compound which forms an ester of nitrous acid in the reaction system may also be used. It may also be advantageous to use an alcohol along with a nitrogen compound selected from the group consisting of nitrogen monoxide, nitrogen dioxide, dinitrogen trioxide and dinitrogen tetraoxide, and hydrates of a nitrogen oxide instead of an ester of nitrous acid by introducing a gas containing molecular oxygen into the system in cases where nitrogen monoxide is used. As the hydrates of a nitrogen oxide may effectively be used nitric acid, nitrous acid and the like. An alcohol to be used in such cases is selected from alcohols which constitute esters of nitrous acid as mentioned hereinbelow.

The catalyst used in the present process is one in which metallic palladium or a salt thereof is carried on such an inert carrier as active carbon, alumina, silica, diatomaceous earth, pumice, zeolite, molecular sieve and the like.

The palladium to be used need not necessarily be pure and a noble metal containing palladium as a main component may also be used. As the palladium salts may be mentioned an inorganic salt such as nitrate, sulfate, phosphate, halide, etc., and an organic acid salt such as acetate, oxalate, benzoate, etc. Palladium complex salts may also be used for the purpose. The amount of palladium to be carried on a carrier is in the range of 0.01 to 10% by weight calculated on metallic palladium and it is usually sufficient to carry it in an amount of 0.5 to 2% by weight.

The preferable ester of nitrous acid used in the process of this invention is an ester of nitrous acid with a saturated monohydric aliphatic alcohol having 1 to 8 carbon atoms or an alicyclic alcohol having 1 to 8 carbon atoms. As the alcohol component may be mentioned an aliphatic alcohol such as methanol, ethanol, n-propanol, isopropanol, n-butanol, isobutanol, sec-butanol, tert-butanol, n-amyl alcohol, isoamyl alcohol, hexanol, octanol, etc., and an alicyclic alcohol such as cyclohexanol, methylcyclohexanol, etc. These alcohols may contain therein a substituent such as an alkoxy group which does not inhibit the reaction.

While the amount of ester of nitrous acid to be used may be changed over a wide range, it is necessary to make exist the ester of nitrous acid in the reaction system so that its concentration in the gaseous material which is introduced into the reactor may be not less than 1% by volume.

The higher the concentration of an ester of nitrous acid is, the more speedily the reaction proceeds. However, the upper limit may necessarily be selected so that a liquid phase of a diester of oxalic acid may not be accumulated in the reaction zone. The ester of nitrous acid is used usually in an amount of 5 to 20% by volume.

Carbon monoxide to be used in the process of this invention may be pure or may be diluted with an inert gas such as nitrogen, etc. The concentration of carbon monoxide in the reaction zone may vary over a wide range and usually is in the range of 20 to 90% by volume.

In the process of this invention, when relatively high concentration of an ester of nitrous acid is used, the reaction proceeds in sufficiently high speed even at a considerably low temperature, and the lower the reaction temperature is, the less side-products are formed. In such a case, however, the reaction is inhibited when a liquid phase is formed in the reaction zone. Accordingly, it is advantageous to carry out the reaction at relatively low temperature while maintaining the desired space time yield. The reaction temperature preferably is in the range of 50° to 200° C. The reaction pressure may be in a range where a liquid phase is not accumulated in the reaction zone. While ordinary pressure may usually be sufficient, the reaction system may be under slightly higher pressure or under slightly reduced pressure depending upon the starting material.

The process of this invention is practiced by using a reactor of fixed bed or fluidized bed. The contact time during which a gaseous material contacts with a solid catalyst is not more than 10 seconds, preferably 0.2 to 5 seconds.

Next, Examples of this invention will be illustrated. In Tables 1 to 4, BN means n-butyl nitrite; DBO means di-n-butyl oxalate; DBC means di-n-butyl carbonate; BA means n-butyraldehyde; BF means n-butyl formate; BL means n-butyraldehyde di-n-butyl acetal and BuOH means n-butanol.

EXAMPLES 1 to 6

In a tubular reactor made of glass and having an inside diameter of 25 mm. and a length of 550 mm., there was packed 18.5 g (30 ml.) of a granular catalyst of 0.95 mm. in diameter in which 0.92% by weight of palladium was carried on a carbon. On the granular carbon catalysts thus packed were loaded Raschig rings made of glass in a height of 150 mm. along the tube. The tubular reactor was fixed vertically and a coiled electric heater was mounted outside the reactor to adjust the temperature inside the catalyst layer by heating to a predetermined one. A starting material, n-butyl nitrite, was supplied by a constant delivery pump to a carburettor heated by an oil bath.

On the other hand, carbon monoxide was supplied to the carburettor at a predetermined flow rate and introduced from the top of the tubular reactor into the catalyst layer together with the vaporized n-butyl nitrite. The reaction products passed through the catalyst layer were collected in a trap cooled by ice water and a trap cooled by dry-ice-methanol, and then analyzed by gas chromatography. The results are shown in Table 1.

TABLE 1

| Ex. No. | reaction conditions: temperature of catalyst layer (°C.) | contact time (second) | CO supply (l./hr.) | BN (raw material): purity* (%) | supply (g./hr.) | conversion of BN (%) | output (mmol./hr): DBO | DBC | BA | BF | BL | space time yield of DBO (g./l. hr.) |
|---|---|---|---|---|---|---|---|---|---|---|---|---|
| 1 | 85 | 2.8 | 30 | 91.0 | 9.85 | 53.9 | 15.3 | 0.74 | 0.05 | 0.17 | 0.03 | 103 |
| 2 | 110 | 2.6 | 30 | 86.4 | 9.24 | 88.5 | 31.0 | 1.56 | 1.73 | 2.00 | 0.17 | 209 |
| 3 | 129 | 2.5 | 30 | 86.4 | 10.3 | 98.5 | 34.3 | 2.20 | 5.18 | 5.10 | 0.43 | 231 |
| 4 | 135 | 2.3 | 30 | 90.5 | 16.3 | 99.1 | 50.4 | 4.30 | 16.8 | 15.9 | 0.44 | 339 |
| 5 | 159 | 2.3 | 30 | 95.0 | 9.42 | 99.5 | 23.2 | 2.69 | 18.3 | 16.4 | 0.09 | 159 |
| 6 | 132 | 0.9 | 81 | 90.8 | 15.8 | 84.5 | 42.1 | 2.30 | 9.20 | 8.77 | 0.97 | 283 |

*Greater part of impurities is occupied by BuOH.

EXAMPLES 7 to 10

In the tubular reactor for gaseous phase reaction under ordinary pressure which was used in Examples 1 to 6, there were packed 6.22 g. (10 ml.) of granular catalysts of 0.95 mm. in diameter in which 0.92% by weight of palladium was carried on carbon granules. Then, experiments were conducted in the same manner by using as a starting material a mixture of predetermined amounts of n-butyl nitrite and n-butanol and by introducing further a gaseous mixture of predetermined amounts of molecular oxygen and carbon monoxide. The results are shown in Table 2.

TABLE 2

| Ex. No. | reaction conditions: temp. of catalyst layer (°C.) | contact time (second) | CO supply (l./hr.) | $O_2$ supply (l./hr.) | gaseous mixture of BN & BuOH (raw material): concentration of BN (%) | supply (l./hr.) | conversion of BN (%) | output (mmol./hr.): DBO | DBC | BA | BF | BL | space time yield of DBO (g./l.hr.) |
|---|---|---|---|---|---|---|---|---|---|---|---|---|---|
| 7 | 124 | 0.71 | 30 | 1.0 | 20.1 | 8.66 | 86.2 | 3.88 | 0.34 | 0.01 | 0.63 | 0.59 | 78 |
| 8 | 127 | 0.71 | 30 | 1.0 | 40.3 | 8.81 | 71.8 | 12.3 | 0.78 | 0.17 | 1.30 | 0.45 | 249 |
| 9 | 132 | 0.70 | 30 | 1.0 | 74.9 | 9.14 | 178.3 | 22.5 | 78.3 | 1.53 | 1.40 | 0.13 | 454 |

TABLE 2-continued

| Ex. No. | reaction conditions: temp. of catalyst layer (°C.) | contact time (second) | CO supply (l./hr.) | $O_2$ supply (l./hr.) | gaseous mixture of BN & BuOH (raw material): concentration of BN (%) | supply (l./hr.) | conversion of BN (%) | output (mmol./hr.): DBO | DBC | BA | BF | BL | space time yield of DBO (g./l.hr.) |
|---|---|---|---|---|---|---|---|---|---|---|---|---|---|
| 10 | 130 | 0.69 | 30 | 1.0 | 96.6 | 10.1 | 88.5 | 32.8 | 1.71 | 2.56 | 2.56 | — | 662 |

EXAMPLES 11 and 12

In the apparatus for gaseous phase reaction under ordinary pressure which was used in Examples 1 to 6, the tubular reactor was packed with 8.62 g. (10 ml.) of columned pellet catalysts (manufactured by Nippon Engerhard Co., Ltd.) of 3 mm. in diameter and of 4 mm. in height in which 0.5% by weight of palladium was carried on a carrier, followed by introduction of n-butanol, nitrogen monoxide, molecular oxygen and carbon monoxide as starting materials in gaseous phases into the catalyst layer.

EXAMPLE 13

In the apparatus for gaseous phase reaction under ordinary pressure which was used in Examples 1 to 6, the tubular reactor was packed with 6.2 g. (10 ml.) of granular catalysts of 0.95 mm. in diameter in which 0.92% by weight of palladium was carried on carbon, followed by introduction of starting materials, i.e., n-butanol, carbon monoxide and a 64% aqueous solution of nitric acid in gaseous phases into the catalyst layer.

The results of Examples 11 to 13 are shown in Table 3.

EXAMPLES 14 to 16

A pressure tube made of stainless steel (SUS 304) and having an inside diameter of 25 mm. and a length of 700 mm. was packed with 6.15 g. (10 ml.) of granular catalysts of 0.95 mm. in diameter in which 0.92% by weight of palladium was carried on carbon. Upon the catalyst were placed Raschig rings made of glass in a height of 200 mm. along the length of the reactor. The thus packed layers were heated at a predetermined temperature from outside of the tube by a coiled electric heater. A starting material, n-butyl nitrite, was supplied through a nozzle at the top of the tubular reactor by using a constant delivery pump, vaporized by heating together with carbon monoxide and then introduced into the catalyst layer. The gas which passed through the catalyst layer was cooled and condensed to give a reaction liquid. Gas which was not condensed was discharged by reducing the pressure to ordinary pressure while maintaining the pressure of the reaction system to be a predetermined value and adjusting the flow of gas to be a predetermined rate. The thus obtained reaction liquid was analyzed by gas chromatography. The results are shown in Table 4.

TABLE 3

| Ex. No | reaction conditions: temp. of catalyst layer (°C.) | contact time (second) | supply of raw material: CO (l./hr.) | $O_2$ (l./hr.) | N source (l./hr.) | BuOH (g./hr.) | conversion of BuOH (%) | output (mmol./hr.): DBO | DBC | BA | BF | BL | space time yield of DBO (g./hr.) |
|---|---|---|---|---|---|---|---|---|---|---|---|---|---|
| 11 | 131 | 0.62 | 30 | 1.4 | $NO_2$ 2.8 | 8.43 | 29.5 | 9.68 | 2.22 | 6.15 | 5.20 | 0.80 | 196 |
| 12 | 130 | 0.72 | 30 | 0.7 | $NO_2$ 2.8 | 8.55 | 18.6 | 1.79 | 0.69 | 1.39 | 0.92 | 0.01 | 36 |
| 13 | 136 | 0.76 | 30 | 0.7 | $HNO_3$ 1.9 | 6.92 | 36.2 | 3.46 | 0.19 | 2.90 | 2.15 | 0.02 | 70 |

TABLE 4

| Ex. No | reaction conditions: pressure (Kg./cm²G) | temp. of catalyst layer (°C.) | contact time (second) | CO supply (l./hr.) | BN (raw material): purity* of BN (%) | supply (g./hr.) | conversion of BN (%) | output (mmol./hr.): DBO | DBC | BA | BF | BL | space time yield of DBO (g./l.hr.) |
|---|---|---|---|---|---|---|---|---|---|---|---|---|---|
| 14 | 2.0 | 157 | 0.61 | 110 | 77.8 | 14.2 | 97.1 | 32.9 | 2.12 | 16.7 | 12.6 | 0.18 | 664 |
| 15 | 5.0 | 153 | 0.62 | 220 | 76.9 | 14.3 | 58.4 | 18.8 | 1.29 | 5.76 | 6.32 | 0.16 | 380 |
| 16 | 10.0 | 150 | 0.57 | 440 | 77.6 | 11.7 | 46.9 | 11.2 | 0.93 | 2.61 | 3.30 | 0.14 | 225 |

*Greater part of impurities is occupied by BuOH.

EXAMPLES 17 to 24

In the apparatus for gaseous phase reaction under ordinary pressure which was used in Examples 1 to 6, the tubular reactor was packed with a predetermined palladium-carrying catalyst, and carbon monoxide and a predetermined ester of nitrous acid were introduced thereinto to subject the reactant to catalytic reaction. The reaction products were collected by cooling and then analyzed by gas chromatography. The results are shown in Table 5.

TABLE 5

| | reaction conditions | | | | | | | diester of oxalic acid | |
|---|---|---|---|---|---|---|---|---|---|
| Ex. No. | amount of catalyst (mml.) | temp. of catalyst layer (°C.) | contact time (second) | ester of nitrous acid name of ester and purity (%)* | | supply (g./hr.) | CO supply (l./hr.) | output (mmol./hr.) | space time yield (g./l.) hr.) |
| 17 | 2% Pd—$SiO_2$ 30 | 169-173 | 1.8 | methyl nitrite | 49.0 | 21.3 | 30 | 70.9 | 279 |
| 18 | 2% Pd—$SiO_2$ 30 | 170-171 | 3.1 | ethyl nitrite | 70.0 | 29.6 | 12 | 50.6 | 246 |
| 19 | 5% Pd—C 30 | 118-114 | 2.2 | isobutyl nitrite | 59.3 | 22.5 | 30 | 4.9 | 33 |
| 20 | 2% Pd—$SiO_2$ 30 | 163 | 1.9 | isopropyl nitrite | 91.5 | 26.9 | 30 | 68.6 | 398 |
| 21 | 2% Pd—$SiO_2$ 30 | 168 | 1.9 | tert-butyl nitrite | 92.8 | 28.2 | 30 | 1.2 | 8 |
| 22 | 5% Pd—C 30 | 163-167 | 1.9 | cyclohexyl nitrite | 90.5 | 15.8 | 30 | 11.3 | 96 |
| 23 | 2% Pd—$SiO_2$ 30 | 157-163 | 2.3 | n-octyl nitrite | 92.3 | 13.0 | 30 | 12.0 | 126 |
| 24 | 2% $PdCl_2$—C 30 | 125-139 | 2.3 | n-butyl nitrite | 90.0 | 14.5 | 30 | 29.1 | 196 |

*Greater part of impurities is an alcohol corresponding to the alcohol component constituting respective esters of nitrous acid.

We claim:

1. A process for preparing a diester of oxalic acid which comprises contacting an ester of nitrous acid with carbon monoxide in the gaseous phase under ambient or reduced pressure in the presence of a solid catalyst containing metallic palladium or a salt thereof at a temperature of 50° to 200° C., [and] *said* ester of nitrous acid being an ester of nitrous acid with an alcohol having 1 to 8 carbon atoms selected from the group consisting of a saturated monohydric [alphatic] *aliphatic* alcohol and an alicyclic alcohol, to produce the diester of oxalic acid containing the same ester group as that of said ester of nitrous acid.

2. The process of claim 1, wherein a gas containing molecular oxygen is added to the gaseous reaction mixture.

3. The process of claim 1, wherein an alcohol having 1 to 8 carbon atoms selected from the group consisting of a saturated monohydric alcohol and an alicyclic alcohol is added to the gaseous reaction mixture.

*4. A process for preparing a diester of oxalic acid which comprises bringing, in a zone in which a liquid phase is not accumulated, carbon monoxide together with a vaporized ester of nitrous acid in a gaseous phase into contact with a solid catalyst containing metallic palladium or a salt thereof at a temperature of 50° to 200° C. and under a pressure in the range where a liquid phase is not accumulated in said zone, said ester of nitrous acid being an ester of nitrous acid with an alcohol having 1 to 8 carbon atoms selected from the group consisting of a saturated monohydric aliphatic alcohol and an alicyclic alcohol, to produce in said zone the diester of oxalic acid containing the same ester group as that of said ester of nitrous acid.*

*5. The process of claim 4 wherein said zone is under a pressure from ordinary pressure to about 10 kg/cm²G.*

*6. The process of claim 4 wherein said zone is under a pressure from ordinary pressure to about 5 kg/cm²G.*

*7. The process of claims 4, 5 or 6, wherein a gas containing molecular oxygen is added to said gaseous phase.*

*8. The process of claims 4, 5 or 6, wherein an alcohol having 1 to 8 carbon atoms selected from the group consisting of a saturated monohydric alcohol and an alicyclic alcohol is added to said gaseous phase.*

*9. The process of claim 4 wherein the ester of nitrous acid is fed to said zone.*

* * * * *